US011839858B1

(12) United States Patent
Beason et al.

(10) Patent No.: US 11,839,858 B1
(45) Date of Patent: *Dec. 12, 2023

(54) PERACETIC ACID CONCENTRATION AND MONITORING AND CONCENTRATION-BASED DOSING SYSTEM

(71) Applicant: Zee Company I, LLC, Chattanooga, TN (US)

(72) Inventors: George Beason, Chattanooga, TN (US); Jonathon R. Bullard, Chattanooga, TN (US); James A. Faller, Chattanooga, TN (US); Robert C. Bullard, Signal Mountain, TN (US)

(73) Assignee: Zee Company I, LLC, Chattanooga, TN (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/196,587

(22) Filed: Mar. 9, 2021

Related U.S. Application Data

(63) Continuation of application No. 15/436,210, filed on Feb. 17, 2017, now Pat. No. 10,974,211.

(Continued)

(51) Int. Cl.
*A23L 3/3454* (2006.01)
*B01F 23/40* (2022.01)
(Continued)

(52) U.S. Cl.
CPC ............... *B01F 23/49* (2022.01); *A23B 4/12* (2013.01); *A23L 3/3508* (2013.01); *A61L 2/18* (2013.01);
(Continued)

(58) Field of Classification Search
None
See application file for complete search history.

(56) References Cited

U.S. PATENT DOCUMENTS 2,347,434 A 4/1944 Reichert et al.
2,377,038 A 5/1945 Reichert et al.
(Continued)

FOREIGN PATENT DOCUMENTS

CA 2569025 6/2008
DK 84296 C 1/1958
(Continued)

OTHER PUBLICATIONS

Bauermeister et al., "Validating the Efficacy of Peracetic Acid Mixture as an Antimicrobial in Poultry Chillers", J. of Food Protection, vol. 71, No. 6, 2008, pp. 1119-1122.
(Continued)

*Primary Examiner* — Paul S Hyun
(74) *Attorney, Agent, or Firm* — DeWitt LLP

(57) ABSTRACT

A system and related methods for monitoring and dosing peroxycarboxylic acids, particularly peracetic acid, in food processing applications based upon desired concentration of the processing solution. The concentration of the peroxycarboxylic acid measured and additional peroxycarboxylic acid being added to the processing solution if the measured concentration is below a threshold level of the desired concentration, and additional water being added to the processing solution if the measured concentration is above a threshold level of the desired concentration. The system and related methods capable of being used in utilized with either live stream or static, storage tank based systems, to keep the concentration of peroxycarboxylic acid at or near desired concentration levels while experiencing less variation than experienced with conventional flow-based or hand-mixed systems.

30 Claims, 3 Drawing Sheets

Related U.S. Application Data

(60) Provisional application No. 62/299,276, filed on Feb. 24, 2016, provisional application No. 62/296,373, filed on Feb. 17, 2016.

(51) Int. Cl.
| | |
|---|---|
| *A23B 4/12* | (2006.01) |
| *G01N 31/00* | (2006.01) |
| *A23L 3/3508* | (2006.01) |
| *A61L 2/18* | (2006.01) |
| *B01F 35/21* | (2022.01) |
| *B01F 35/22* | (2022.01) |
| *B01F 101/48* | (2022.01) |

(52) U.S. Cl.
CPC ...... *B01F 35/2132* (2022.01); *B01F 35/2202* (2022.01); *G01N 31/00* (2013.01); *A23V 2002/00* (2013.01); *B01F 23/483* (2022.01); *B01F 2101/48* (2022.01)

(56) References Cited

U.S. PATENT DOCUMENTS

| | | | |
|---|---|---|---|
| 2,512,640 A | 6/1950 | Greenspan et al. | |
| 2,966,415 A | 12/1960 | Rinehart et al. | |
| 3,104,170 A | 9/1963 | Mahon et al. | |
| 3,104,978 A | 9/1963 | Elder | |
| 3,122,417 A | 2/1964 | Blaser et al. | |
| 3,234,140 A | 2/1966 | Irani et al. | |
| 3,689,283 A | 9/1972 | May et al. | |
| 4,675,947 A | 6/1987 | Clatfelter et al. | |
| 5,069,922 A | 12/1991 | Brotsky et al. | |
| 5,139,788 A | 8/1992 | Schmidt | |
| 5,143,739 A | 9/1992 | Bender et al. | |
| 5,200,189 A | 4/1993 | Oakes et al. | |
| 5,208,057 A | 5/1993 | Greenley | |
| 5,234,703 A | 8/1993 | Guthery | |
| 5,283,073 A | 2/1994 | Bender et al. | |
| 5,364,650 A | 11/1994 | Guthery | |
| 5,435,808 A | 7/1995 | Holzhauer et al. | |
| 5,462,713 A | 10/1995 | Schlitzer et al. | |
| 5,489,434 A | 2/1996 | Oakes et al. | |
| 5,567,444 A | 10/1996 | Hei et al. | |
| 5,597,791 A | 1/1997 | Richards et al. | |
| 5,632,676 A | 5/1997 | Kurschner et al. | |
| 5,635,231 A | 6/1997 | Bender et al. | |
| 5,674,538 A | 10/1997 | Lokkesmoe et al. | |
| 5,718,910 A | 2/1998 | Oakes et al. | |
| 5,720,983 A | 2/1998 | Malone | |
| 5,863,244 A | 1/1999 | Mansfield | |
| 5,965,033 A | 10/1999 | Huss et al. | |
| 6,008,405 A | 12/1999 | Gray et al. | |
| 6,010,729 A | 1/2000 | Gutzmann et al. | |
| 6,103,286 A | 8/2000 | Gutzmann et al. | |
| 6,113,963 A | 9/2000 | Gutzmann et al. | |
| 6,183,807 B1 | 2/2001 | Gutzmann et al. | |
| 6,284,719 B1 | 9/2001 | Simms | |
| 6,342,528 B1 | 1/2002 | McKenzie et al. | |
| 6,455,086 B1 | 9/2002 | Trinh et al. | |
| 6,514,556 B2 | 2/2003 | Hilgren et al. | |
| 6,518,419 B1 | 2/2003 | Van Der Lugt et al. | |
| 6,527,872 B1 | 3/2003 | Fricker et al. | |
| 6,534,075 B1 | 3/2003 | Hei et al. | |
| 6,545,047 B2 | 4/2003 | Gutzmann et al. | |
| 6,558,620 B1 | 5/2003 | Sanford et al. | |
| 6,582,961 B1 | 6/2003 | Moon et al. | |
| 6,605,253 B1 | 8/2003 | Perkins | |
| 6,627,593 B2 | 9/2003 | Hei et al. | |
| 6,627,657 B1 | 9/2003 | Hilgren et al. | |
| 6,964,788 B2 | 11/2005 | Phebus et al. | |
| 7,077,967 B2 | 7/2006 | Perkins et al. | |
| 7,387,736 B2 | 6/2008 | Phillips et al. | |
| 7,470,655 B2 | 12/2008 | Biering et al. | |
| 7,754,670 B2 | 7/2010 | Lange et al. | |
| 7,767,240 B2 | 8/2010 | Howarth | |
| 7,832,360 B2 | 11/2010 | Hilgren et al. | |
| 7,887,641 B2 | 2/2011 | Man et al. | |
| 8,020,520 B2 | 9/2011 | Hilgren et al. | |
| 8,029,693 B2 | 10/2011 | Dada et al. | |
| 8,030,351 B2 | 10/2011 | Gutzmann et al. | |
| 8,043,650 B2 | 10/2011 | Gutzmann et al. | |
| 8,057,812 B2 | 11/2011 | Man et al. | |
| 8,128,976 B2 | 3/2012 | Man et al. | |
| 8,246,758 B2 | 8/2012 | Man et al. | |
| 8,372,461 B2 | 2/2013 | Bullard et al. | |
| 8,877,254 B2 | 11/2014 | Li et al. | |
| 8,916,510 B2 | 12/2014 | Gutzmann et al. | |
| 9,497,964 B2 | 11/2016 | Dagher et al. | |
| 10,912,321 B2 | 2/2021 | Harvey et al. | |
| 10,974,211 B1 * | 4/2021 | Beason | A23B 4/20 |
| 11,350,640 B1 | 6/2022 | Bullard et al. | |
| 2001/0044401 A1 | 11/2001 | Perkins et al. | |
| 2002/0072627 A1 | 6/2002 | Chandalia et al. | |
| 2002/0083549 A1 | 7/2002 | Dietermann | |
| 2003/0047087 A1 | 3/2003 | Phebus et al. | |
| 2003/0148727 A1 | 8/2003 | Hilgren et al. | |
| 2003/0180385 A1 | 9/2003 | Martinelli et al. | |
| 2003/0199583 A1 | 10/2003 | Gutzmann et al. | |
| 2003/0200997 A1 | 10/2003 | Gill et al. | |
| 2003/0211169 A1 | 11/2003 | Tabasso | |
| 2005/0209120 A1 | 9/2005 | Reinhardt et al. | |
| 2005/0245416 A1 | 11/2005 | Veening et al. | |
| 2006/0113506 A1 | 6/2006 | Man et al. | |
| 2006/0225439 A1 | 10/2006 | Morris, III et al. | |
| 2006/0286227 A1 | 12/2006 | Terry | |
| 2007/0025897 A1 | 2/2007 | Rheingans et al. | |
| 2007/0244261 A1 | 10/2007 | Fukui et al. | |
| 2007/0269563 A1 | 11/2007 | Mixon et al. | |
| 2007/0292580 A1 | 12/2007 | Gutzmann et al. | |
| 2009/0043123 A1 | 2/2009 | Copenhafer et al. | |
| 2009/0143481 A1 | 6/2009 | Man et al. | |
| 2009/0145859 A1 | 6/2009 | Man et al. | |
| 2009/0282847 A1 | 11/2009 | Bullard et al. | |
| 2009/0311134 A1 | 12/2009 | Iwashita et al. | |
| 2009/0324790 A1 | 12/2009 | Hilgren et al. | |
| 2010/0021557 A1 | 1/2010 | Li et al. | |
| 2010/0075883 A1 | 3/2010 | Geret et al. | |
| 2010/0092574 A1 | 4/2010 | Sweeny | |
| 2010/0108942 A1 | 5/2010 | Man et al. | |
| 2010/0196503 A1 | 8/2010 | Heisig et al. | |
| 2010/0227000 A1 | 9/2010 | Ames et al. | |
| 2010/0323037 A1 | 12/2010 | Curry et al. | |
| 2011/0027383 A1 | 2/2011 | Hilgren et al. | |
| 2011/0135534 A1 | 6/2011 | Bates et al. | |
| 2011/0177145 A1 | 6/2011 | Erkenbrecher, Jr. et al. | |
| 2011/0220155 A1 | 9/2011 | Man et al. | |
| 2011/0274766 A1 | 11/2011 | Allen et al. | |
| 2011/0305805 A1 | 12/2011 | Gutzmann et al. | |
| 2011/0311691 A1 | 12/2011 | Gutzmann et al. | |
| 2012/0165407 A1 | 6/2012 | Gupta et al. | |
| 2012/0244261 A1 | 9/2012 | Harvey et al. | |
| 2012/0245228 A1 | 9/2012 | Harvey et al. | |
| 2012/0322872 A1 | 12/2012 | Kraus et al. | |
| 2013/0251819 A1 | 9/2013 | Knueven et al. | |

FOREIGN PATENT DOCUMENTS

| | | |
|---|---|---|
| EP | 0564250 A2 | 10/1993 |
| EP | 0564250 A3 | 10/1993 |
| EP | 0550137 | 12/1996 |
| EP | 0985349 | 3/2000 |
| EP | 1199931 | 7/2003 |
| EP | 1435203 | 7/2004 |
| GB | 947688 | 1/1964 |
| GB | 1456592 | 11/1976 |
| GB | 2289676 | 11/1995 |
| JP | H08165298 | 6/1996 |
| WO | WO9406294 | 3/1994 |
| WO | WO9421122 | 9/1994 |
| WO | WO9424869 | 11/1994 |
| WO | WO9742984 | 11/1997 |
| WO | WO 99/00025 | 1/1999 |
| WO | WO0105255 | 1/2001 |

(56) References Cited

FOREIGN PATENT DOCUMENTS

| WO | WO0237972 | 5/2002 |
|---|---|---|
| WO | WO 02/054866 A1 | 7/2002 |
| WO | WO02060280 | 8/2002 |
| WO | WO03092919 | 11/2003 |
| WO | WO2006015626 | 2/2006 |
| WO | WO 2007/092087 A2 | 8/2007 |
| WO | WO 2009/027857 A1 | 3/2009 |
| WO | WO2009156972 | 12/2009 |
| WO | WO2012037294 | 3/2012 |

OTHER PUBLICATIONS

Bell, "Reduction of doodborne mirco-organisms on beef carcass tissue using acetic acid, sodium bicarbonate, and hydrogen peroxide spray washes", Food Microbiology (1997), 14, 439-448.
Carciofi et al., "Water uptake by poultry carcasses during cooling by water immersion", Chemical Engineering and Processing: Process Intensification, vol. 46, No. 5, 2007, pp. 444-450.
Dorn, "Examination of *Salmonella* Decontamination of Broiler Carcasses", 1988, 28 pages.
Gusev, "Peracetic Acid for Salmonella Decontamination in Poultry Carcasses", Veterinary Disease Control Review (2007), 4 pages.
Harris et al., "Microbiological and organoleptic characteristics of beef trim and ground beef treated with acetic acid, lactic acid, acidified sodium chlorite, or sterile water in a simulated commercial processing environment to reduce *Escherichia coli* O157:H7 and *Salmonella*", Meat Science, 90, 2012, pp. 783-788.
Joseph, "Meat Decontamination", University of Bristol (1997), pp. 1, 8-9, 12, 33-35, 38, 43, 64-91, 98-99 and 104-105.
Labadie, "Development of a New Technique for Obtaining Axenic Meat", European J. Appl. Microbiol. (1977), 4, 67-73.
Mohan et al. "Role of Peroxyacetic Acid, Octanoic Acid, Malic Acid, and Potassium Lactate on the Microbiological and Instrumental Color Characteristics of Ground Beef", J. Food Science, vol. 77, No. 4, 2012, pp. M188-M193.
Nationalchickencouncil.org (Food Safety and Inspection in the U.S. Broiler Chicken Industry).
Quilo et al., "Microbial, instrumental color and sensory characteristics of inoculated ground beef produced using potassium lactate, sodium metasilicate or peroxyacetic acid as multiple antimicrobial interventions", Meat Science, 84, 2010, pp. 470-476.
Russell, "Solving the Yield/Pathogen Reduction Dilemma", Watt 290 Poultry USA, Oct. 2007, pp. 30-34.
Bauermeister, L.J. et al., "The Microbial and Quality Properties of Poultry Carcasses treated with Peracetic Acid as Antimicrobial Treatment", Department of Poultry Science. © 2008 Poultry Science Association, Inc. Retrieved Feb. 25, 2008. Accepted Jun. 13, 2008. 9 pages.
Li, Junzhong et al., File History of U.S. Appl. No. 61/427,952, filed Dec. 29, 2010, titled "In Situ Generation of Peroxycarboxylic Acids at Alkaline pH, and Methods of Use Thereof".
Alvarado, C. et al., "Marination to Improve Functional Properties and Safety of Poultry Meat", Department of Animal and Food Sciences. © 2007 Poultry Science Association, Inc. 15 pages.
Yuan, Z. et al., "Kinetics of Paracetic Acid Decomposition Part 1: Spontaneous Decompostion at Typical Pulp Bleaching Conditions", The Canadian Journal of Chemical Engineering. vol. 75. Feb. 1997. 6 pages.
Baldry, M.G.C. et al., "The Activity of Peracetic Acid in Sewage Indicator Bacteria and Viruses", Wat.Sci. Tech, vol. 24, No. 2, pp. 353-357. © 1991.
Ercken,D. et al.., "Effects of Peracetic Acid and Monochloramine on the Inactivation of Naegleria Lovaniesis", Water Science Technology. vol. 47, No. 3, pp. 167-171. © 2003.
Schmidt, Ronald H., "Basic Elements of Equipment Cleaning and Sanitizing in Food Processing and Handling Operations", University of Florida. 11 pages. Publication FS14, Dec. 12, 2018.

Artés, F. et al., "Improved Strategies for Keeping Overall Quality of Fresh-cut Produce", Proc. IC on Qual. Manag. Fresh Cut Produce. 2007, pp. 245-258.
Chandra, Sofia Santi, "Effects of Low-dose Gamma Irradiation, Chlorine, and Peroxyacetic Acid (PAA) on Fresh Sliced Radish", A Research Project, Submitted to the Graduate Faculty of Chapman Univeristy. Aug. 2004. 56 pages.
Ernst, C. et al., "Efficacy of Amphoteric Surfactant-and Peracetic Acid-Based Disinfectants on Spores of *Bacillus cereus* In Vitro and on Food Premises of the German Armed Forces", Journal of Food Protection. vol. 69, No. 7, pp. 1605-1610, 2006.
Rodrigues, Laura Beatriz, et al., "Quantification of Biofilm Production on Polystyrene by *Listeria, Escherichia coli* and *Staphylococcus aureus* Isolated From a Poultry Slaughterhouse", Brazilian Journal of Microbiology (2010) 41: 1082-1085.
Sánchez-Ruiz, Concepción, et al., "An Evaluation of the Efficiency and Impact of Ray Wastewater Disinfection with Peracetic Acid Prior to Ocean Discharge", Wat. Sci. Tech. vol. 32, No. 7 pp. 159-166. 1995.
Trachoo, Nathanon, "Survival of *Campylobacter jejuni* in Biofilms Isolated from the Water System of a Chicken House", A Dissertation submitted to the Graduate Faculty of The University of Georgia in Partial Fulfillment of t he Requirements for the Degree Doctor of Philosophy. Athens, Georgia. 2001.
Vij, Shilpa, "New Sanitation Technologies", pp. 125-128 from Lecture Compendium: Advances in Cleaning and Sanitation in Food Industry, The Seventeenth Short Course, Centre of Advanced Studies, Division of Dairy Technology, National Dairy Research Institute, Mar. 3-23, 2004.
Howarth, Jon, "PERASAN® Efficacy Against *Listeria monocytogenes* and *E. coli* in 15% Salt Brine Solutions of 40° F.", EnviroTech. Feb. 15, 2005.4 pages.
Baert, Leen, et al., "Efficacy of Sodium Hypochlorite and Peroxyacetic Acid To Reduce Murine Norovirus 1, B40-8, *Listeria monocytogenes,* and *Escherichia coli* O157:H7 on Shredded Iceberg Lettuce and in Residual Wash Water", Journal of Food Protection. vol. 27, No. 5 (2009). pp. 1047-1054.
Baldry, M.G.C., "The Bactericidal, Fungicidal and Sporicidal Properties of Hydrogen Peroxide and Peracetic Acid", Journal of Applied Bacteriology, pp. 417-423. 1983.
Burfoot, Dean, et al., "Reducing Microbial Counts on Chicken and Turkey Carcasses Using Lactic Acid", ScienceDirect. Food Control 22 (2011) pp. 1729-1735.
Dickens, J.A., et al., "Effects of Acetic Acid and Hydrogen Peroxide Application During Defeathering on the Microbiological Quality of Broiler Carcasses Prior to Evisceration", Poultry Science 76:657-660 (1997).
Dickens, J.A., et al., "The Effects of Extended Chilling Times with Acetic Acid on the Temperature and Microbiological Quality of Processed Poultry Carcasses", Processing and Products. Poultry Science 74:1044-1048 (1995).
Dorsa, Warren J., et al., "Long-Term Bacterial Profile of Refrigerated Groudn Beef Made from Carcass Tissue, Experimentally Contaminated with Pathogens and Spoilage Bacteria after Hot Water Alkaline, or Organic Acid Washes", Journal of Food Protection, vol. 61, No. 12 pp. 1615-1622 (1998).
foodsmatter.com., www.foodsmatter.com/miscellaneous_articles/misc_articles/research/bleach_and_vinegar.html, "Improving Bleach's Bug-killing Potential". First published in Jul. 2009.
Gill, C.O., et al., "Effects of Peroxyacetic Acid, Acidified Sodium Chlorite or Lactic Acid Solutions on the Microflora of Chilled Beef Carcasses", International Journal of Food Microbiology 91 (2004) pp. 43-50.
Kemp, G. Kere, et al., "Acidified Sodium Chlorite Antimicrobial Treatment of Boiler Carcasses", Journal of Food Protection. vol. 63, No. 8 (2000) pp. 1087-1092.
Lillard, H.S., "Effect of Trisodium Phosphate of Salmonellae Attached to Chicken Skin", Journal of Food Protection. vol. 57, No. 6. pp. 465-469. Jun. 1994.
Peracetic Acid Technical Report, Peracetic Acid Processing, CAS No. 79-21-0, NOSB TAP Review Compiled by OMRI, Last updated Nov. 3, 2000 (7 pages).

(56) References Cited

OTHER PUBLICATIONS

*Zeco, LLC, d/b/a Company* v. *Enviro Tech Chemical Services, Inc.*, Amended Complaint for Declaratory Judgement In the United States Direct Court Eastern Direct of Tennessee at Chattanooga, Case No. 1:21-cv-00079-CEA-CHS, Document 95, filed Aug. 30, 2022. 21 pages.
Simpson, Catherine A. et al. "Antimicrobial Ingredients" Chapter 14 from Ingredients in Meat Products, pp. 301-377 (2009).
Application and File History for U.S. Appl. No. 15/436,210, filed Feb. 17, 2017, now U.S. Pat. No. 10,974,211 issued on Apr. 13, 2021, inventors Beason et al.
Application and File History for U.S. Appl. No. 15/676,622, filed Aug. 14, 2017, now U.S. Pat. No. 11,350,640 issued on Jun. 7, 2022, inventors Beason et al.
Bottemiller, Helena, "Russia Agrees to Lift Ban on U.S. Poultry Imports", Jun. 25, 2010. https://www.foodsafetynews.com/2010/06/russia-agrees-to-lift-ban-on-us-poultry-imports/.
Young et al., Moisture Retention by Water-and Air-Chilled Chicken Broilers During Processing and Cutup Operations; 2004, pp. 119-122, Poultry Science Association, Inc.
May et al., Effect of Phosphate Treatment on Carcass-Weight Changes and Organoleptic Quality of Cup-Up-Chicken; 1962, pp. 24-32, University of Georgia, and Market Quality Research Division, AMS, USDA Georgia.
nationalchickencouncil.org, "Food Safety and Inspection in the U.S. Broiler Chicken Industry", (2013). http://www.nationalchickencouncil.org/industry-issues/food-safety/, 2 pages.

\* cited by examiner

PERACETIC ACID CONCENTRATION AND MONITORING AND CONCENTRATION-BASED DOSING SYSTEM

CROSS-REFERENCE TO RELATED APPLICATIONS

The present application is a continuation of U.S. application Ser. No. 15/436,210 filed Feb. 17, 2017 which claims the benefit of U.S. Provisional Application No. 62/296,373, filed Feb. 17, 2016, and U.S. Provisional Application No. 62/299,276, filed Feb. 24, 2016, both of which are hereby incorporated herein in their entirety by reference.

TECHNICAL FIELD

The present invention relates to the field of wash and sterilization products for reducing microbial activity in protein food products intended for human consumption. More specifically, the present invention is directed to apparatus and related methods for monitoring and dosing peracetic acid based upon desired solution.

BACKGROUND

The world population has grown to point where mass production of the foods that we consume is no longer a luxury but a requirement. Local farmers, providing food and food products directly to the marketplace, cannot meet the demands of modern society. The food supply chain now incorporates very large, complex farms and high speed and very high volume processing plants to satisfy the need for mass processing and production of food. Maintaining a safe food supply chain relies on the dedication of those working in the supply chain, the processing plants and also on the third party oversight of various Federal agencies whose regulations support and mandate food safety.

With two major exceptions, the physical process of taking an animal from the farm to the consumer has changed very little over time. The introduction of refrigeration, and the implementation of various chemistries to help maintain sanitary conditions and to control microbiology, has given modern food processors an advantage not enjoyed by food producers of a century ago. Refrigeration and chemical intervention practices have become an integral part of food processing facility operations. These technologies have enabled the high speed, high volume output of the large processing facilities that could not have been possible in times past without significant concern for consumer safety. With large scale and continuous processing methods being employed by large processors of protein products, or any other product that is susceptible to microbiological contamination, the concern for the control of microbiology and the safety of the food supply chain is of paramount importance.

One of the main concerns in slaughtering and processing plants is unwanted microorganisms that are emitted into the air or are contained on the animal carcass when the animal is processed, such as four-legged animals or red meat (i.e., beef, pork, etc.) and poultry (i.e., turkey, duck and chicken) during shackling, killing, scalding, and picking areas. The microorganisms that may become airborne or contained on the animal carcass are unwanted in the processing and packing areas of the plant because they can affect product quality and safety. They also pose a potential threat to the health and well-being of the workers in the plant. Still further, such microorganisms can affect down-field processes in a processing plant, posing quality and safety concerns to the ultimate consumer of the poultry product.

The use of antimicrobial agents on red meat has been implemented to control microbial growth. PAA, which is also sometimes called peracetic acid or peroxyacetic acid, is a peroxycarboxylic acid and is a well known chemical for its strong oxidizing potential, has the molecular formula $CH_3COOOH$, and has a molecular structure as follows:

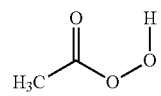

An equilibrium peroxyacetic acid solution is produced from an equilibrium mixture of hydrogen peroxide, acetic acid and water ("equilibrium PAA solution"), which often uses an acid catalyst, e.g., sulfuric acid.

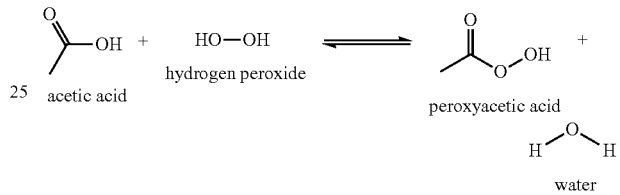

Based on the nature of the equilibrium equation, the ability to maintain appropriate concentrations of PAA can be difficult as the microbiological load is continually changing within dispensing systems. As such, it would be advantageous to improve upon existing peroxycarboxylic acid systems, including PAA systems, so as to maintain peroxycarboxylic acid concentrations, such as PAA concentrations, at appropriate concentrations without continually adding the respective peroxycarboxylic acid in excess.

SUMMARY

While the following description relates to PAA, it is contemplated that such systems may also be utilized by other peroxycarboxylic acids have 2 to 20 carbon atoms, such as peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and combinations and mixtures thereof.

Representative embodiments of the present invention utilize a PAA monitoring system so as to measure PAA concentrations in real-time and allow for PAA concentration control within a much tighter concentration range than using commercially available PAA determination methods. Generally, the PAA monitoring systems of the present invention can include a PAA probe capable of instantaneously measuring and transmitting a PAA concentration signal to a control system. The control system can log and record PAA concentrations so as to track system performance. In addition, the control system can control one or more injection systems, for example, a PAA dosing/metering pump system, to add additional PAA when the measured PAA concentration is below a threshold level and/or a metering pump system to add water or other solution when the measured PAA concentration exceeds the threshold level. In this way, the PAA concentration level in a given fluid-environment can be kept at or near desired concentration levels while experiencing less variation than experienced with conventional flow-based or hand-mixed systems.

In one representative embodiment, the present invention can comprise a live stream application in which PAA is added directly to a water stream to form a PAA solution for immediate use in sanitizing/wash systems. Generally, a fresh water inlet stream can be provided with an injection port for a concentrated PAA solution. The fresh water and concentrated PAA solution can be mixed within an inline static mixer to form a PAA solution for use in the sanitizing/wash system. A sample stream can be pulled from the PAA solution and directed through a PAA monitoring system, whereby a PAA probe can instantly measure a PAA concentration in the PAA solution. The PAA probe transmits a signal to a controller that indicates the PAA concentration of the PAA solution. Based on the PAA concentration, the controller can selectively operate a PAA dosing pump to either pump or cease pumping the concentrated PAA solution into the fresh water inlet stream based on a threshold level of the PAA concentration that was previously programmed into the controller.

In another representative embodiment, the present invention can comprise a static system application in which one or more storage tanks are used to store a PAA solution for use in a sanitizing/wash system. Generally, the one or more storage tanks can be fluidly connected to an inlet stream, a process stream, a sampling stream and an adjustment stream. The inlet stream can comprise a water inlet stream and can optionally include PAA added with the live stream application. The process stream generally takes a PAA solution from within the storage tank for use in a sanitizing/wash process at a point of use. The sample stream continually samples a small amount of the PAA solution within the storage tank and directs said sample PAA solution through a PAA monitoring system. Within the PAA monitoring system, a PAA probe can instantly measure a PAA concentration in the sample PAA solution to determine PAA concentration within the storage tank. The PAA probe transmits a signal to a controller that indicates the PAA concentration of the PAA solution within the storage tank. Based on the PAA concentration, the controller can selectively operate a PAA dosing system to pump additional amounts of a concentrated PAA solution into the storage tank when a threshold level of the PAA concentration is less than desired. Alternatively, the controller can selectively operate a water supply to add additional amounts of water into the storage tank when a threshold level of the PAA concentration is greater than desired. In this way, PAA concentration within the storage tank can be maintained at desired levels and ready for instant operation even if a sanitizing/wash process is offline.

In yet another representative embodiment, the present invention can comprise a PAA monitoring system that can be utilized with either live stream or static, storage tank based systems. Generally, a sample stream can be provided to a 3-way valve that provides for either a sampling stream to be directed past a PAA probe or a diversion stream that directs the sample stream to drain or alternatively, back to a source of the sample stream. If the live or static system is active, the sampling stream is directed past a PAA probe can instantly measure a PAA concentration in a PAA solution to determine PAA concentration within the live or static system. The PAA probe transmits a signal to a controller associated with the live or static system that indicates the PAA concentration of the PAA solution within live or static system. Based on the PAA concentration, the controller can selectively operate a PAA dosing system and/or water supply in the liver or static system to adjust the PAA concentration based on a desired PAA threshold value. When the live or static system is offline, the 3-way valve diverts the sample stream through the diversion stream and around the PAA probe so as to avoid unintended dilutions of or spikes in PAA concentration within the sample stream such that the PAA monitoring system is ready to instantly resume accurate operation when the sanitizing/wash associated with the live stream or static system is brought back online.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
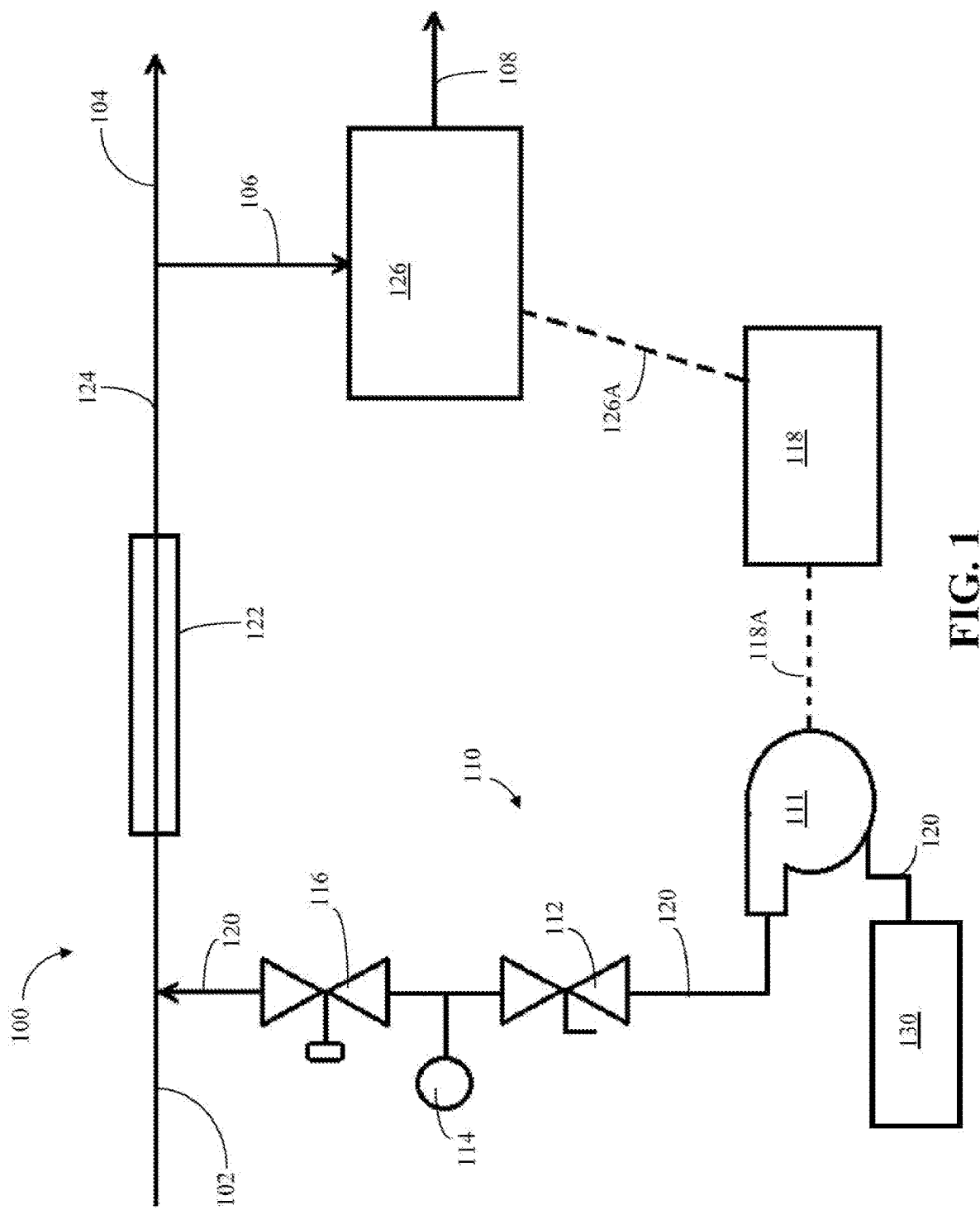
FIG. 1 is a schematic illustration of a live stream PAA dosing and monitoring system according to an embodiment of the present invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

As illustrated in FIG. 1, an inline PAA supply system 100 can be utilized to supply a PAA solution to various soaking, dipping, quenching, rinsing, spraying or washing systems for food processing. Generally PAA supply system 100 can comprise a fresh water inlet stream 102, a PAA dosing stream 120, a PAA solution outlet stream 104, a PAA sampling stream 106 and a sample drain stream 108. Generally, fresh water inlet stream 102 can be supplied with water from a municipal or private water source that is supplied to the PAA supply system at a desired pressure. In some aspects, the desired pressure is in the pressure range of about 14.1 psi to about 100 psi. The municipal or private water source can be filtered and otherwise treated prior to use. Generally, PAA dosing stream 120 can be fed from a dosing/metering pump assembly 110 having a dosing/metering pump 111, a check valve 112, a pressure gauge 114 and a backpressure regulator 116. The dosing/metering pump assembly 110 can comprise a metering pump 111 operably connected to a PAA chemical supply 130, wherein the metering pump 111 is selectively operated at the direction of a control assembly 118. Control assembly 118 can comprise a programmable logic controller or similar processor based controller. At the direction of a signal 118A from the control assembly 118, the dosing/metering pump 111 supplies a concentrated PAA stream 120 from the chemical supply 130 into the fresh water inlet stream 102 at a point upstream of a static mixer 122. The static mixer 122 thoroughly mixes the fresh water inlet stream 102 and the concentrated PAA stream 120 to form a PAA solution stream 124.

As the PAA solution stream 124 leaves the static mixer 122, a portion is pulled off as the PAA sampling stream 106 and supplied to a PAA monitoring system 126. The PAA monitoring system 126 can comprise a suitable PAA concentration sensor such as, for example, PAA probes available from ProMinent® Dosiertechnik Gmbh of Heidelberg, Germany or Analytical Technology of Delph Saddleworth, United Kingdom. Generally, the concentration of PAA within the PAA solution steam 124 will be targeted to be about 300 ppm and can fluctuate between about 285 ppm to about 360 ppm. One of ordinary skill in the art will appreciate other targeted concentrations can be utilized, such as a targeted concentration between about 10 ppm to about 2500 ppm. One of ordinary skill will also appreciation there may be an acceptable fluctuation from the targeted concentration. In some aspects, the acceptable fluctuation is about −5% to about +20%, in some other aspects about −4% to about +15%, in some other aspects about −3% to about +10% from the targeted concentration. In some aspects, the acceptable fluctuation is about −5% to about 0% from the targeted concentration. In some aspects, the acceptable fluctuation is about +20% to about 0% from the targeted concentration.

As the PAA concentration sensor of the PAA monitoring system 126 measures the concentration of PAA within the PAA solution stream 124 via the PAA sampling stream 106, a signal 126A, for example, a 4-20 mA analog signal, indicating the PAA concentration level is sent to the control assembly 118. If the concentration of PAA within the PAA solution stream is less than the targeted level of about 300 ppm, the control assembly 118 will direct the dosing/metering pump assembly 110 to supply additional amounts of the concentrated PAA stream 120 into the fresh water inlet stream 102. By continually monitoring and adjusting PAA concentration levels in the PAA solution stream 124, the concentration of PAA within the PAA solution outlet stream 104 is maintained close to the desired level and can continually be relied upon for use with downstream soaking, dipping, quenching, rinsing, spraying or washing systems for food processing applications. Following measuring of the PAA concentration within the PAA sampling stream 106 by the PAA monitoring system 126, the PAA sampling stream 106 may be discarded as sample drain system 108. PAA supply system 100 can be utilized to directly supply a food processing application (i.e., soaking, dipping, quenching, rinsing, spraying or washing system) in real-time.

Figure 2:
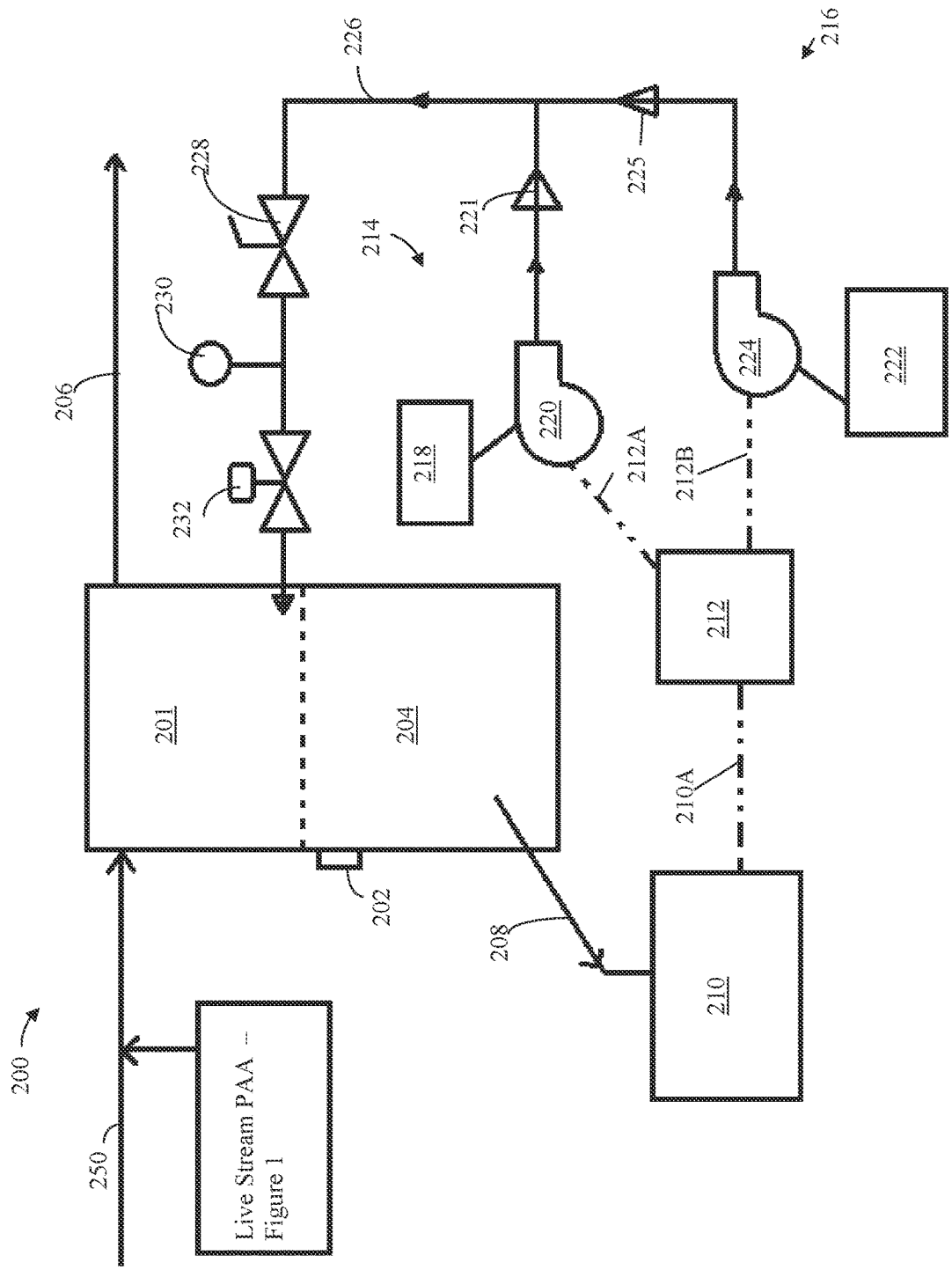
FIG. 2 is a schematic illustration of a static stream PAA dosing and monitoring system according to an embodiment of the present invention.

In an alternative embodiment, a static PAA supply system 200 can be used to maintain PAA concentrations within a storage tank 201 as shown in FIG. 2, wherein the storage tank 201 is used to supply the soaking, dipping, quenching, rinsing, spraying or washing system with a process PAA stream 206. Storage tank 201 can comprise a level sensor 202 so as to maintain a desired volume of PAA solution 204 within the storage tank 201 (the desired volume represented by the dotted line). Generally, a process PAA stream 206 is supplied from the storage tank 201 and will go to a point of use. Because of the nature of the PAA equilibrium reaction, the concentration of PAA within the PAA solution 204 must be continually monitored to ensure that suitable amounts of PAA are supplied within the process PAA stream 206. In order to continually monitor the PAA solution 204 within the storage tank 201, a tank sampling stream 208 is pulled from the storage tank 201 and evaluated by a PAA monitoring system 210. The PAA monitoring system 210 utilizes a suitable PAA sensor such as, for example, PAA probes available from ProMinent® Dosiertechnik Gmbh of Heidelberg, Germany or Analytical Technology of Delph Saddleworth, United Kingdom, to test the PAA concentration in the tank sampling stream 208, which is representative of the PAA concentration level in the PAA solution 204. For example, it may be desired to have a targeted PAA concentration of 300 ppm in the PAA solution 204, wherein the PAA concentration may then vary between about 285 ppm to about 360 ppm in the storage tank 201. One of ordinary skill in the art will appreciate other targeted concentrations can be utilized, such as a targeted concentration between about 10 ppm to about 2500 ppm. One of ordinary skill will also appreciate that the system may provide an acceptable fluctuation from the targeted concentration. In some aspects, the acceptable fluctuation is about −5% to about +20%, in some other aspects about −4% to about +15%, in some other aspects about −3% to about +10% from the targeted concentration. In some aspects, the acceptable fluctuation is about −5% to about 0% from the targeted concentration. In some aspects, the acceptable fluctuation is about +20% to about 0% from the targeted concentration.

As the PAA monitoring system 210 measures the PAA concentration level in the tank sampling stream 208, the PAA monitoring system 210 communicates with a controller 212, for example, a programmable logic controller or similar processor based controller, and communicates a signal 210A, for example a 4-20 mA signal, of PAA concentration to the controller 212. Based on the measured PAA concentration level, controller 212 selectively operates a tank water supply system 214 or a tank PAA supply system 216. Tank water supply system 214 generally comprises a water source 218, a water pump 220 and a water check valve 221. Tank PAA supply system 216 generally comprises a PAA source 222, a PAA dosing/metering pump 224 and a PAA check valve 225.

If the PAA monitoring system 210 measures a PAA concentration level in the tank sampling stream 208 that exceeds the threshold or target PAA level of about 300 ppm, the controller 212 operably turns on the water pump 220 whereby water is added to the tank through an adjustment stream 226 that comprises a shut off valve 228, a pressure gauge 230 and a back pressure regulator 232. In some aspects, controller 212 sends a signal 212A to the tank water supply system 214 or the water pump 220. If the PAA monitoring system 210 measures a PAA concentration level in the tank sampling stream 208 that is less than the threshold or target PAA level of about 300 ppm, the controller 212 operably turns on the PAA dosing/metering pump 224 whereby a concentrated PAA solution is added to the tank through the adjustment stream 226. In some aspects, controller 212 sends a signal 212B to the tank PAA supply system 216 or the PAA water dosing/metering pump 224. In this way, the PAA concentration level of PAA solution 204 is maintained at approximately the desired level regardless of the residence time of the PAA solution 204 within the storage tank 201. In this way, PAA concentration within the PAA solution 204 will always have suitable levels of PAA regardless of potential off-gassing within the storage tank 201 or due to natural equilibrium changes.

In some aspects, the storage tank 201 is fed an initial amount of PAA solution from the main supply 250 comprising the PAA solution outlet stream 104 described in FIG. 1. Once the initial amount of PAA is provided in the storage tank 204, the adjustment stream 226 maintains and/or adjusts the concentration of the PAA solution 204 maintained within the storage tank 204. In some other aspects, the main supply 250 comprises the PAA solution outlet stream 104 described in FIG. 1, the flow rate of which into the storage tank 204 is about equal to the flow rate of the process PAA stream 206 out of the storage tank 204. In some other aspects, the level of PAA solution 204 within the storage tank 201 is maintained only by the adjustment stream 226 after the storage tank 201 reaches its initial volume level of PAA solution 204.

In some other aspects, the main supply 250 initially comprises fresh water to fill the storage tank 201, such that the adjustment stream 226 is needed to reach the desired concentration level of the PAA solution 204 within the storage tank 201. In some aspects, after the desired concentration level of the PAA solution 204 is achieved, the adjustment stream 226 is then utilized to maintain and/or adjust the concentration of the PAA solution 204 while maintained within the storage tank 201.

In yet some other aspects, the main supply 250 may comprise a combination of fresh water and the PAA solution outlet stream 104 described in FIG. 1, such that the desired concentration level of the PAA solution 204 within the storage tank 201 is maintained and/or adjusted by the adjustment stream 226.

Figure 3:
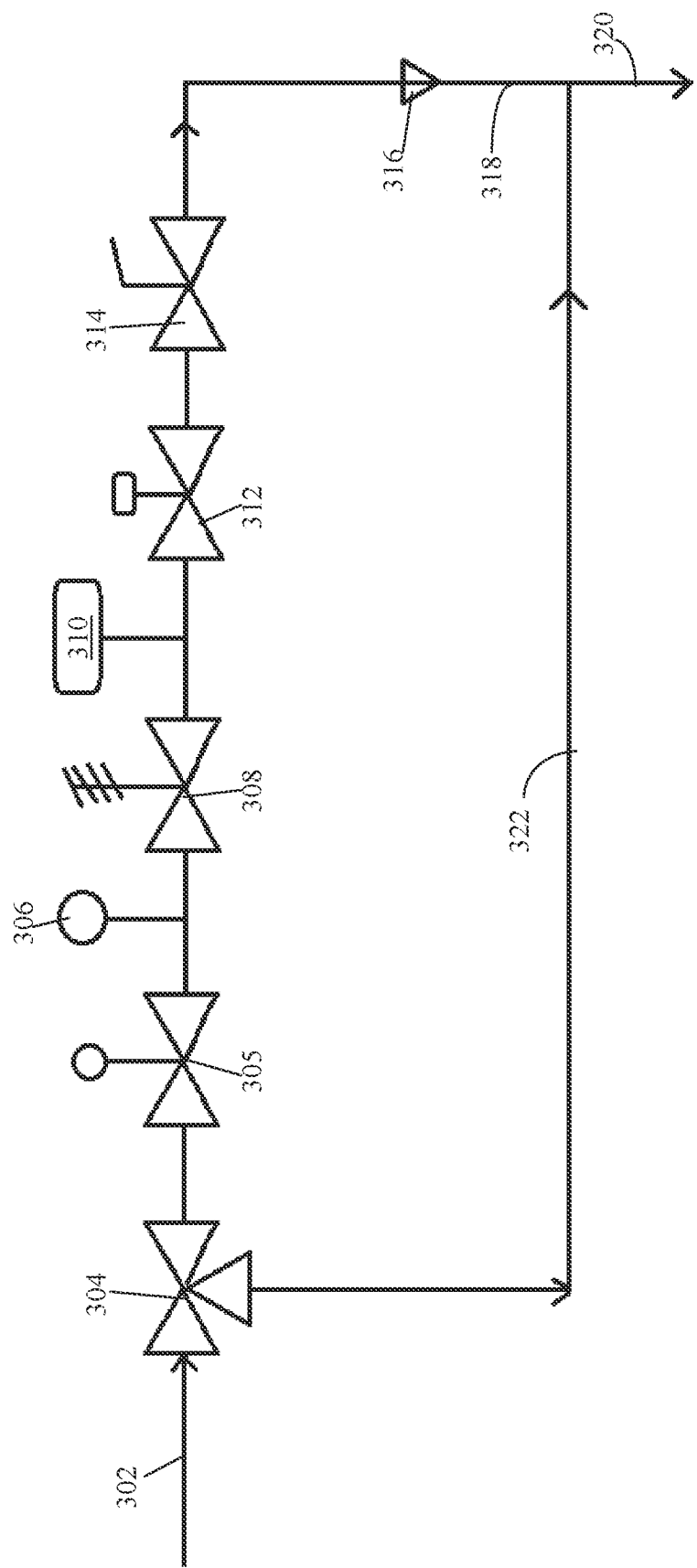
FIG. 3 is a schematic illustration of a PAA monitoring system according to an embodiment of the present invention.

PAA monitoring system 126 and/or PAA monitoring system 210 can take the form of PAA monitoring system 300 as illustrated in FIG. 3. Generally, PAA monitoring system 300 can comprise an inlet sample stream 302, a 3-way valve 304, a pressure regulator 305, a flowmeter 306, a relief vent 308, a PAA probe 310, a flow regulator 312, a shut-off valve 314 and a check valve 316. Following sampling, sample stream 318 can be directed to drain or back to a process through outlet sample stream 320. At time when the wash process is offline or otherwise shut down, the inlet sample stream 302 can be diverted around the PAA probe 310 through the use of the 3-way valve 304 so as to divert the inlet sample stream 302 through a sample divert stream 322. In this way, build ups of water or unintended spikes in PAA concentration can be avoided in the inlet sample stream 302 when the wash process is brought back online.

Generally, the PAA monitoring system 300 functions by directing the inlet sample stream 302 past the PAA probe 310. PAA probe 310 can comprise a suitable PAA probe such as, for example, PAA probes available from ProMinent® Dosiertechnik Gmbh of Heidelberg, Germany or Analytical Technology of Delp Saddleworth, United Kingdom. The PAA probe 310 generally measures PAA concentration and converts said measurement into a suitable signal, for example, a 4-20 mA analog signal, whereby said signal is transmitted for use by a controller, such as, for example, control assembly 118 or controller 212.

While the foregoing inline PAA supply system 100, static PAA supply system 200, and PAA monitoring system 126, 210 and/or 300 have been described relating to PAA, it is contemplated that other peroxycarboxylic acids can be monitored using the same or similar systems, including equilibrium peroxycarboxylic acid solutions or pH modified peroxycarboxylic acid solutions. In such configurations, PAA probe 310 would be comprise a suitable probe to measure the respective peroxycarboxylic acid(s) concentration and convert said measurement into a suitable signal, much like that described for the PAA probe 310. In some aspects, the peroxycarboxylic acid solution is chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and combinations and mixtures thereof.

The equilibrium peroxycarboxylic acid, such as peroxyacetic acid, preferably has a pH above about 3.0 and below about 7.0, in some aspects about 3.5 to about 5.5, and in some other aspects about 3.5 to about 5.0, although subranges within these ranges are contemplated.

In certain aspects of the present invention, the pH modified peroxycarboxylic acid is prepared using at least one buffering agent, said at least one buffering agent chosen from sodium hydroxide, potassium hydroxide, sodium salts of carbonic acid, potassium salts of carbonic acid, phosphoric acid, silicic acid and combinations thereof.

The pH modified peroxycarboxylic acid preferably has a pH above about 7.0 and below about 10.0, in certain aspects a pH range of about 7.0 to about 9.5, and in some other aspects a pH range of about 7.5 to about 9.0, although subranges within these ranges are contemplated. The pH modified peroxycarboxylic acid can be prepared by combining a peroxycarboxylic acid solution, such as a peroxyacetic acid solution, with one or more buffering agents chosen from sodium hydroxide, potassium hydroxide, the sodium salt of carbonic acid, the potassium salt of carbonic acid, phosphoric acid, silicic acid or mixtures thereof, in a quantity that is necessary to bring the solution to said pH range One of ordinary skill in the art will appreciate that other alkalizing chemistries approved for direct food contact may also be used, whether alone or in combination with any of the foregoing buffering agents. The quantity of the buffering agent in a buffered peroxycarboxylic acid solution will generally be in the range of about 0.01% to about 10% by volume of the total solution, but other volumes of the buffering agent may be utilized depending upon various parameters, such as local water condition, including pH, hardness and conductivity.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system for controlling a desired concentration of peroxycarboxylic acid in a processing solution for use in a food product processing application, the system comprising:
   a mixer tank comprising a processing solution comprising water and a concentration of peroxycarboxylic acid, the mixer tank in fluid communication with a main supply inlet stream comprising a stream of processing solution, an adjustment inlet stream, and a processing solution outlet stream;
   a mixer disposed in fluid communication with the mixer tank, wherein the mixer is configured to receive and mix an inlet stream comprising water and a second adjustment inlet stream comprising a peroxycarboxylic acid solution to provide the main supply inlet stream fed to the mixer tank;
   a probe in fluid communication with at least a portion of the processing solution, the probe configured to measure the concentration of peroxycarboxylic acid of the processing solution, and the probe is capable of transmitting a signal relating to a measured peroxycarboxylic acid concentration of the processing solution;
   a control assembly configured to receive the signal from the probe and determine whether the measured peroxycarboxylic acid concentration is between an upper threshold concentration level of a desired concentration of peroxycarboxylic acid of the processing solution and below a lower threshold concentration level of the desired concentration of peroxycarboxylic acid of the processing solution by comparing the measured peroxycarboxylic acid concentration to the upper and lower threshold concentration levels, wherein the desired concentration of peroxycarboxylic acid of the processing solution is between 10 ppm and 2500 ppm, wherein the lower threshold concentration level is in a range from greater than 0% to about 5% less than the desired concentration of peroxycarboxylic acid, and wherein the upper threshold concentration level is in a range from greater than 0% to about 20% greater than the desired concentration of peroxycarboxylic acid; and
   a dosing assembly configured to be selectively operated by the control assembly to either increase or decrease a concentration of peroxycarboxylic acid to the adjustment inlet stream to provide the processing solution within the mixer tank having the desired concentration of peroxycarboxylic acid, wherein the dosing assembly is configured to be controlled by the control assembly to increase the concentration of peroxycarboxylic acid in the adjustment inlet stream when the measured concentration of peroxycarboxylic acid of the processing solution is below the lower threshold concentration level, and wherein the dosing assembly is configured to be controlled by the control assembly to decrease the concentration of peroxycarboxylic acid in the adjustment inlet stream when the measured concentration of peroxycarboxylic acid of the processing solution is above the upper threshold concentration level; and
   wherein the processing solution outlet stream from the mixer tank is provided downstream from the mixer tank to one or more food products to reduce antimicrobial activity on the one or more food products.

2. The system of claim 1, further comprising a second probe in fluid communication with a sample stream that is in fluid communication with the mixer, the sample stream configured to comprise at least a portion of the main supply inlet stream from the mixer prior to being introduced into the mixer tank, the probe configured to measure the concentration of the peroxycarboxylic acid in the sample stream, and the probe capable of transmitting a signal relating to a measured peroxycarboxylic acid concentration of the main supply inlet stream.

3. The system of claim 2, further comprising a second control assembly configured to receive the signal from the second probe and determine whether the measured peroxycarboxylic acid concentration is between the upper and lower threshold concentration levels by comparing the measured peroxycarboxylic acid concentration to the upper and lower threshold concentration levels.

4. The system of claim 3, further comprising a second dosing assembly configured to be selectively operated by the second control assembly, wherein the second dosing assembly is configured to be controlled by the second control assembly to add additional peroxycarboxylic acid in the second adjustment inlet stream when the measured concentration of peroxycarboxylic acid of the main supply inlet stream is below the lower threshold concentration level, and wherein the second dosing assembly is configured to be controlled by the control assembly to stop adding peroxycarboxylic acid in the second adjustment inlet stream when the measured concentration of peroxycarboxylic acid of the main supply inlet stream is above the upper threshold concentration level.

5. The system of claim 1, wherein the mixer is a static mixer.

6. The system of claim 1, wherein the measured concentration of peroxycarboxylic acid of the processing solution is from a processing solution sample stream configured to be provided from the mixer tank.

7. The system of claim 1, wherein the dosing assembly comprises a dosing pump configured to add a concentrated peroxycarboxylic acid solution to the adjustment inlet stream.

8. The system of claim 1, wherein the dosing assembly is further configured to be controlled by the control assembly to increase an amount of water added to the adjustment inlet stream when the measured concentration of the peroxycarboxylic acid processing solution is above the upper threshold concentration level.

9. The system of claim 8, wherein the dosing assembly comprises a water pump configured to add water to the adjustment inlet stream.

10. The system of claim 1, wherein the peroxycarboxylic acid comprises equilibrium peracetic acid.

11. The system of claim 1, wherein the peroxycarboxylic acid is chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and combinations and mixtures thereof.

12. The new system of claim 1, wherein the peroxycarboxylic acid comprises pH modified peracetic acid having a pH in a range between 7.5 and 9.0.

13. The system of claim 1, wherein the desired concentration of the peroxycarboxylic acid is between about 10 ppm and about 2000 ppm.

14. The system of claim 1, wherein the desired concentration of the peroxycarboxylic acid is between about 100 ppm and about 2000 ppm.

15. The system of claim 1, wherein the lower threshold concentration level is less than about 5% of the desired concentration, or the upper threshold concentration level is greater than about 20% of the desired concentration.

16. The system of claim 1, wherein the processing solution comprises peracetic acid and at least one buffering agent, such that the processing solution has a pH greater than 7.0.

17. The system of claim 1, wherein the processing solution has a pH less than about 10.0.

18. The system of claim 1, wherein the processing solution comprises peracetic acid and at least one buffering agent in a range of about 0.01% to about 10% by volume.

19. The system of claim 1, wherein the lower threshold concentration level is about 4% less than the desired concentration of peroxycarboxylic acid of the processing solution.

20. The system of claim 1, wherein, the upper threshold concentration level is about 15% greater than the desired concentration of peroxycarboxylic acid of the processing solution.

21. The system of claim 1, wherein the probe is in fluid communication with a processing solution sample stream that is in fluid communication with the mixer tank, the probe configured to measure the concentration of peroxycarboxylic acid in the processing solution sample stream, and the probe is capable of transmitting a signal relating to the measured peroxycarboxylic acid concentration.

22. The system of claim 1, wherein the range of the lower threshold concentration level is from about 3% to about 5% less than the desired concentration of peroxycarboxylic acid of the processing solution.

23. The system of claim 1, wherein the range of the upper threshold concentration level is from about 10% to about 20% greater than the desired concentration of peroxycarboxylic acid of the processing solution.

24. The system of claim 1, wherein the peroxycarboxylic acid comprises equilibrium peracetic acid, and wherein the desired concentration of the peracetic acid is between 10 ppm and 2000 ppm.

25. The system of claim 24, wherein the desired concentration of the peracetic acid is between 100 ppm and 2000 ppm.

26. The system of claim 24, wherein the lower threshold concentration level is less than about 5% of the desired concentration, or the upper threshold concentration level is greater than about 20% of the desired concentration.

27. The system of claim 1, wherein the processing solution comprises peracetic acid and at least one buffering agent, such that the processing solution has a pH greater than 7.0 and less than 10.0.

28. The system of claim 27, wherein the desired concentration of the peracetic acid is between 10 ppm and 2000 ppm.

29. The system of claim 28, wherein the desired concentration of the peracetic acid is between 100 ppm and 2000 ppm.

30. The system of claim 28, wherein the lower threshold concentration level is less than about 5% of the desired concentration, or the upper threshold concentration level is greater than about 20% of the desired concentration.

* * * * *